United States Patent [19]

Kosaka et al.

[11] Patent Number: 4,554,249

[45] Date of Patent: Nov. 19, 1985

[54] METHOD FOR THE QUANTITATIVE DETERMINATION OF PHYSIOLOGICAL COMPONENTS IN BIOLOGICAL FLUIDS

[75] Inventors: Akira Kosaka, Seto; Sawao Murao, Sakai; Kenichi Hirano, Iwakura; Noriaki Tanaka, Sakai; Kuniyoshi Matsunaga, Ichinomiya, all of Japan

[73] Assignee: Amano Pharmaceutical Company Limited, Japan

[21] Appl. No.: 436,385

[22] Filed: Oct. 25, 1982

[30] Foreign Application Priority Data

Feb. 18, 1982 [JP] Japan .................................. 57-25613
Jul. 23, 1982 [JP] Japan ................................. 57-127632
Jul. 23, 1982 [JP] Japan ................................. 57-127633

[51] Int. Cl.$^4$ ..................... C12Q 1/60; C12Q 1/54; C12Q 1/62; C12Q 1/26; C12Q 1/25; C12N 9/02; C07G 17/00; C07G 7/00
[52] U.S. Cl. ........................................ 435/10; 435/11; 435/14; 435/25; 435/28; 435/189; 435/267; 435/269; 436/71; 436/95; 436/97; 436/175; 436/825
[58] Field of Search ................... 435/4, 25, 26, 10, 11, 435/12, 14, 171, 810, 911, 189, 190, 192; 424/94, 177, 230, 238, 315; 436/71, 95, 99, 175

[56] References Cited

U.S. PATENT DOCUMENTS

| | | | |
|---|---|---|---|
| 4,186,251 | 1/1980 | Tarbutton | 435/11 |
| 4,211,844 | 7/1980 | Wu | 435/25 |
| 4,291,121 | 9/1981 | Acquati et al. | 435/10 |
| 4,308,029 | 12/1981 | Siggaard-Andersen | 436/175 |

FOREIGN PATENT DOCUMENTS 1435400  5/1976  United Kingdom ................. 435/11

OTHER PUBLICATIONS

*Clinical Biochemistry: Principles and Methods,* vol. 2, ed. by Curtus, H. Ch. and Roth, M., New York, Walter de Gruyter, (1978), pp. 1372–1374.
Murao, S. and Tanaka, N., "Isolation and Identification of a Microorganism Producing Bilirubin Oxidase", *Agric. Biol. Chem.,* vol. 46, No. 8 (1982), pp. 2031–2034.
Nakamura, T., "Purification and Physico-Chemical Properties of Laccase", *Biochinica et Biophysica Acta,* vol. 39 (1958), pp. 44–52.
Wilkinson, J. H., *The Principles and Practice of Diagnostic Enzymology,* Chicago, Edward Arnold (1976), pp. 553–555.

*Primary Examiner*—Thomas G. Wiseman
*Assistant Examiner*—Joanne Giesser
*Attorney, Agent, or Firm*—McGlew and Tuttle

[57] ABSTRACT

A novel enzyme of bilirubin oxidase produced by a genus Myrothecium or genus Coprinus origin microorganism and a conventional enzyme of laccase are found, in the presence of a specific additive compound, e.g. a surface active agent, aromatic carboxylic acid, sulfa drug or protease, to oxidize both conjugated and unconjugated bilirubin in biological fluid to biliverdin without formation of hydrogen peroxide, such that in the case of conventional enzymatic methods of the quantitative determination of glucose, cholesterol, neutral fats, free fatty acids, phospholipids or uric acid all existing together with bilirubin in biological fluid, the usual interference with such determination, as otherwise caused by bilirubin coexisting in such fluid, can be prevented by adding such a bilirubin oxidase or laccase together with such a specific additive compound to the determinative reaction system.

19 Claims, 6 Drawing Figures

METHOD FOR THE QUANTITATIVE DETERMINATION OF PHYSIOLOGICAL COMPONENTS IN BIOLOGICAL FLUIDS

This invention relates to a method for the quantitative determination of physiological components in biological fluids. More particularly, it relates to a method for the quantitative determination of specific physiological components contained in biological fluids by using bilirubin oxidase either alone or together with supplemental additives. The invention relates further to the same method as above but by using laccase instead of such bilirubin oxidase.

Bilirubin oxidase mentioned above is a novel enzyme, and accordingly the significance of this enzyme may be appreciated by the following detailed preliminary explanation.

Bilirubin ($C_{33}H_{36}N_4O_6$) is a pigment present in biological fluids such as blood serum, urine, etc. An enzyme present in the brain of rats or guinea pigs and an enzyme produced by a mushroom of the genus Agaricus have hitherto been reported to act on bilirubin. However, the enzymological properties of these enzymes have not been elucidated yet.

During a search for microorganisms which produce an enzyme capable of acting on bilirubin, it has been found in connection with the present invention that some microorganisms belonging to the genera Myrothecium and Coprinus produce an enzyme which oxidizes bilirubin. Such microorganisms of the genus Myrothecium include, for example, *Myr. verrucaria* MT-1 (FERM-P 5918) that has newly been isolated in connection with the present invention, and type cultures such as *Myr. verrucaria* IFO 6113, IFO 6133, IFO 6351 and IFO 9056; *Myr. cinctum* IFO 9950; *Myr. roridum* IFO 9531, etc. Such microorganisms of the genus Coprinus include, for example, type cultures such as *Cop. cinereus* IFO 8371, *Cop. lagopides* IFO 30120, etc.

All the microorganisms above mentioned have been deposited in the duly prescribed manner in recognized depositories, to wit, those with the parenthetic abbreviation "FERM" representing deposits thereof in the depository: Fermentation Research Institute, Agency of Industrial Science and Technology (1-3, Higashi 1-chome, Yatabe-machi, Tsukuba-gun, Ibaraki, 305, Japan), and those with the parenthetic abbreviation "IFO" representing deposits thereof in the depository: Institute for Fermentation (17-85, Jusohonmachi 2-chome, Yodogawa-ku, Osaka, 532, Japan).

The taxonomical properties of *Myrothecium verrucaria* MT-1 (FERM-P 5918) are as follows:

1. Morphological characteristics:
   Hyphae: septate, colorless to white, smooth, 1.5~3.0 μm in width.
   Conidia (phialospores): spindle-shaped, fan-shaped substances at end, 2.0~3.0 μm×7.0~8.0 μm.
   Conidiophores: colorless to white.
   Phialides: columnar, 1.5~2.0 μm×11.5~18.0 μm.
2. Cultural characteristics on various media:
   Malt extract agar: growth slightly repressed, flocculent, colorless to white, reverse light yellow to light yellowish grown.
   Potato-glucose agar: growth good, flocculent, colorless to white, reverse light yellowish brown to dim yellow.
3. Physiological characteristics:
   Temperature: growth at 8° C. to 37° C., best at 30° C., no growth at 45° C.
   pH: growth at pH 3.5 to pH 9.5, best at pH 5.0 to pH 7.0.

For preparing the said enzyme by using a microorganism of the genus Myrothecium or Coprinus, the microorganism is cultivated in routine submerged-culture manner and the filtrate of cultured broth is salted out by the addition of ammonium sulfate. The precipitates so formed are dissolved in deionized water to form a solution, which solution is then dialyzed. The inner dialysis solution is, after being decolorized with activated charcoal, subjected to column chromatography and its active fractions which are collected are lyophilized to obtain a powdery preparation. On analyzing the preparation by disc electrophoresis, it was demonstrated that the enzyme protein formed a single band which coincided in position with the enzyme activity.

The enzyme preparation thus obtained was recognized as bilirubin oxidase that oxidized bilirubin to biliverdin ($C_{33}H_{34}N_4O_6$) by an electron acceptor of molecular oxygen. The enzyme is also characterized by no formation of hydrogen peroxide in the course of the oxidation. The enzymological properties of the novel bilirubin oxidase are described below, with the exception that the values shown in parentheses are specifically those of the enzyme of the genus Coprinus origin.

(1) Substrate specificity: Besides bilirubin, the enzyme acts on chlorophyllin and hemin, but does not act on hemoglobin, chlorophyll and vitamin $B_{12}$.
(2) Temperature stability: More than 90% activity is retained at 50° C., while 100% activity is lost at 70° C.
(3) Optimum temperature: 40° C. (30° C.).
(4) pH stability: pH 6-10 (pH 5-9).
(5) Optimum pH: pH 8.
(6) Molecular weight: Approximately 52,000.
(7) Isoelectric point: 4.1 (3.8).
(8) Effect of metal ions: Inhibited markedly by $Fe^{++}$, but not affected by other metal ions.
(9) Inhibitors: Potassium cyanide, sodium azide and thiourea.
(10) Visible light absorption: 1% enzyme solution exhibits no absorption maximum in the vicinity of 375 nm and 460 nm.
(11) Sugar content: Approximately 7.8% as glucose.
(12) Copper content: 1 mole of copper per one mole enzyme.

In addition to the bilirubin oxidase as explained above, studies were further carried out in connection with the present invention on a large number of conventional enzymes. That is, these conventional enzymes were examined to determine whether or not they had the ability to oxidize bilirubin to biliverdin without formation of hydrogen peroxide. As a result, it has been also been found in connection with the present invention that laccase, tyrosinase and ascorbate oxidase have such oxidizing ability, among which laccase is preferred. Currently available preparations of laccase include those originating from a so-called lacquer plant (*Rhus verniciflua*) and from a cultured material of a basidiomycete, e.g. *Polyporus versicolor* IFO 9791 [cf. Biochimica et Biophysica Acta, 30, 44 (1959); Acta Chemica Scandinavica, 21, 2367 (1967)], both of which have ability to oxidize bilirubin to biliverdin.

In accordance with the foregoing, the present invention is concerned with a method for the quantitative determination of specific physiological components contained in biological fluids by using either the bilirubin oxidase which has been prepared as above or the conventional laccase. The physiological components which can be determined by the method of the present invention include bilirubin, glucose, cholesterol, neutral fats, free fatty acids, phospholipids and uric acid. More specifically, according to one feature of the present invention, there is provided a method for the quantitative determination of bilirubin contained in biological fluids by using bilirubin oxidase or laccase. According to another feature of the present invention, there is provided a method for the quantitative determination of physiological components such as glucose, cholesterol, neutral fats, free fatty acids, phospholipids and uric acid all contained in biological fluids, by using bilirubin oxidase or laccase as well as the reagents for use in the conventional method for the determination of said physiological components.

Initially, as described above, according to one feature of the present invention, there is provided a method for the quantitative determination of bilirubin in biological fluids. This method is explained hereinbelow.

Bilirubin is inherently not present in the free state in biological fluids, but present in the form of either so-called conjugated bilirubin (i.e., bilirubin combined with glucuronic acid, sulfuric acid, hydrochloric acid or the like) or so-called unconjugated bilirubin (i.e., bilirubin combined with albumin). It is presently interpreted that conjugated bilirubin increases in cases of liver cell lesion, hepatic jaundice, posthepatic jaundice and the like, whereas unconjugated bilirubin increases in cases of liver dysfunction and the like. Accordingly, it is regarded as necessary to differentially determine both conjugated and unconjugated bilirubin in view of the importance of this information to clinical medicine.

The differential determination of bilirubin has hitherto been conducted by a chemical method in which bilirubin is reacted with a diazo reagent to form azobilirubin, which is then determined colorimetrically. However, the method has the disadvantages of requiring troublesome operations and of lacking in accuracy.

In connection with the present invention the reactivity of bilirubin oxidase as well as laccase with bilirubin present in biological fluids has been studied and accordingly it has been found that while these enzymes, when used alone, may act mainly upon conjugated bilirubin, they have little or no effect on unconjugated bilirubin. That is, as for unconjugated bilirubin, bilirubin oxidase which has been produced by a microorganism of the genus Myrothecium has no effect on it, whereas bilirubin oxidase produced by a microorganism of the genus Coprinus and laccase have a little effect on unconjugated bilirubin.

On the other hand, according to the present invention it has been found further that when the enzymes, the bilirubin oxidase or laccase together with at least one additive selected from the group consisting of surface active agents, aromatic carboxylic acids, sulfa drugs and proteases, are added to a biological fluid containing bilirubin, the above enzymes may act not only upon conjugated bilirubin, but also upon unconjugated bilirubin in the biological fluid, probably because the bond between albumin and bilirubin in the unconjugated bilirubin has been weakened.

In view of the above-mentioned findings according to the present invention, it is elucidated that conjugated bilirubin present in a biological fluid will be able to be determined by using bilirubin oxidase which has been produced by a microorganism of the genus Myrothecium alone, while total bilirubin, that is the sum of conjugated and unconjugated bilirubin both present in the biological fluid, will be able to be determined by using any bilirubin oxidase or laccase together with the said additive. The unconjugated bilirubin level can in this way then readily be calculated by subtracting the former from the latter.

The present method for the differential determination of bilirubin in biological fluids is more specifically explained in the following: Firstly, in substantially the same manner as in the conventional chemical method using a diazo reagent, each of a representative number of individual aqueous solutions of commercially available crystalline bilirubin having varying concentrations, i.e. having successively increasing concentrations from one to the next, is reacted with bilirubin oxidase produced by a microorganism of the genus Myrothecium. For each of the reaction mixtures, the decrease in absorbance at a wavelength of 440 nm or the increase in absorbance at a wavelength of 330 or 380 nm is measured. The measured values are plotted against the corresponding concentrations of said bilirubin solutions to construct a so-called calibration curve representing the relationship therebetween. Then, a biological fluid sample having an unknown bilirubin concentration is caused to react with bilirubin oxidase produced by a microorganism of the genus Myrothecium, and the decrease or increase in absorbance of the reaction mixture is measured. The conjugated bilirubin concentration in the sample is then calculated by comparing the measured value with the calibration curve.

The same procedures as above are conducted except that any bilirubin oxidase or laccase together with the additive(s) as mentioned previously are used in place of only the bilirubin oxidase produced by a microorganism of the genus Myrothecium. Thus, a calibration curve is constructed in the same manner, and the total bilirubin concentration in the sample is calculated from the measured value of absorbance and the calibration curve.

In the method of the determination of total bilirubin, according to the present invention, the bilirubin oxidase of genus Myrothecium or Corinus origin may be used. Similarly, the laccase originating from either a lacquer plant or a cultured material of a basidiomycete may be used. Specific examples of the additive include surface active agents such as sucrose fatty acid esters, sodium cholate, taurocholic acid, sodium dodecyl sulfate, p-toluenesulfonic acid, cetyl pyridinium chloride, nonylphenol ethoxylate and polyoxyethylene-polyoxypropylene condensate; aromatic carboxylic acids such as salicylic acid and sulfosalicylic acid; sulfa drugs such as sulfanilamide and acetosulfamine sodium salt; and proteases such as Pronase P (trademark; mfd. by Kaken Chem. Co.). Among these additives, sodium cholate, taurocholic acid, sodium dodecyl sulfate, p-toluenesulfonic acid, salicylic acid and sulfosalicylic acid are preferred. In the method of the differential determination of bilirubin according to the present invention, buffers, enzyme stabilizers and the like, if necessary may further be used.

The amount of enzyme for use in the present method for the differential determination of bilirubin is such that its concentration in the reaction mixture is equal to 0.003 to 0.40 U/ml for bilirubin oxidase or 0.06 to 7.0 mU/ml for laccase, as expressed by bilirubin oxidase activity the definition of which is set forth hereinafter. The amounts of additives for use are as follows: For example, sodium dodecyl sulfate is used in such an amount as to give a concentration of 0.5 to 10 mM in the reaction mixture and sodium cholate is used in such an amount as to give a concentration of 2 to 30 mM in the reaction mixture.

The unit of the bilirubin oxidase activity is defined as follows: Five mg of bilirubin crystals are dissolved in 250 ml of a 0.2M tris-HCl buffer solution (pH 8.4) containing 1 mM ethylenediaminetetraacetic acid. A 2-ml portion of the resulting solution is mixed with 0.2 ml of an enzyme solution. The mixture is incubated at 37° C. and its absorbance decrease at 440 nm is then measured. Thus, the amount of enzyme which oxidizes 1 micromole of bilirubin per minute is defined as one unit.

Additionally, as described above, according to another feature of the present invention, there is provided a method for the quantitative determination of physiological components such as glucose, cholesterol, neutral fats, free fatty acids, phospholipids and uric acid all contained in biological fluids. This method is explained hereinbelow.

In the field of clinical chemistry, certain known or conventional methods for the quantitative determination of physiological components as above in biological fluids by means of utilizing oxidizing enzymes (e.g. glucose oxidase, cholesterol oxidase, uricase, acylcoenzyme A oxidase, choline oxidase, glycerol-3-phosphate oxidase or the like) have hitherto been conducted. According to these known methods, the hydrogen peroxide which has been formed from a physiological component of interest in the reaction system is decomposed and the absorbance of the reaction mixture is measured. The measured value is compared with the calibration curve which has previously been constructed by using the physiological component in pure form, whereby the concentration of the physiological component in the biological fluid is calculated. However, the said known methods for the determination of physiological components have been subject interfered from other physiological components than the desired component coexisting therewith in the biological fluids. Bilirubin is one of such interfering substances, and while its concentration in the blood serum is not greater than 1 mg/dl in healthy men, it increases to as high as 20 mg/dl in pathological conditions. Thus, a number of methods have heretofore been proposed in order to prevent bilirubin from interfering with the determination of physiological components. By way of example, one such method for this prevention was conducted by adding a ferrocyanate, ascorbic acid, an EDTA-iron complex or a so-called bilirubin-specific fungal enzyme preparation to the reaction system (cf. Jap. Pat. Publn. No. 25840/'80; Jap. Pat. Laid-Open Nos. 29718/'80, 71398/'82 and 151193/'79). However, these prior art techniques had their own disadvantages respectively and could not be regarded as being entirely satisfactory.

It has now been found in accordance with the present invention that when, in carrying out the conventional methods for the quantitative determination of physiological components in biological fluids by utilizing oxidizing enzymes as described above, bilirubin oxidase or laccase together with the said additive(s) are added to the reaction system, the conjugated and unconjugated bilirubin both coexisting in the biological fluids are totally oxidized to an innocuous biliverdin without formation of hydrogen peroxide, whereby the bilirubin is prevented from interfering with the determination of physiological components. It was observed however in this regard that the so-called color-producing substances (e.g. 4-aminoantipyrine, phenol) which are contained in the reagents for use in the conventional methods for the determination of physiological components reacted therein to some extent with the added bilirubin oxidase or laccase resulting in a slight inconvenience in the step of measurement of absorbance. As to such inconvenience, it has been found further in accordance with the present invention that it may be cancelled or overcome by adding sodium fluoride, phenanthroline or hydroxylamine to the reaction system.

The present method for the quantitative determination of physiological components (i.e. glucose, cholesterol, neutral fats, free fatty acids, phospholipids and uric acid) in biological fluids is more specifically explained in the following: Firstly, in substantially the same manner as in the conventional method for the determination of a physiological component of interest, each of a representative number of individual solutions of the component in pure form (crystals, powder or oil) having varying concentrations, i.e. having successively increasing concentrations from one to the next, is reacted with the reagents (including an oxidizing enzyme) for use in the conventional method of the determination of the component of interest, in the presence of bilirubin oxidase or laccase together with said additive as well as, if necessary, sodium fluoride, phenanthroline or hydroxylamine. For each individual resulting reaction mixture, the absorbance at a specific wavelength is measured. The measured values are plotted against the corresponding concentrations of the component solutions to construct a calibration curve representing the relationship therebetween. Then, a biological fluid sample having an unknown concentration of the component is subjected to reaction in the same manner as above, and the absorbance of the reaction mixture is measured. The concentration of the component in the sample is then calculated by comparing the measured value with the calibration curve.

Among the physiological components to be assayed in the present method, neutral fats, free fatty acids and phospholipids are expressed, as seen in the following examples of the invention, as triolein, oleic acid and choline chloride, respectively, as is usual in such cases. The physiological components to be assayed in the present method are all available commercially in any form of crystals, powder or oil, and such commercial preparations were used for the construction of the respective calibration curves in the examples.

In the methods for the determination of physiological components according to the present invention, the bilirubin oxidase used may be of either the genus Myrothecium origin or the genus Coprinus origin. Similarly, the laccase originating from either a lacquer plant or a cultured materials of a basidiomycete may be used. Specific examples of the additive are the same as previously enumerated in connection with the method for the determination of total bilirubin in biological fluids. The amount of bilirubin oxidase or laccase as well as the amount of additives for use in the present method may also both be the same as previously described in connection with the method for the determination of total bilirubin in biological fluids. Sodium fluoride, phenathroline or hydroxylamine is used in such an amount as to give a concentration of 0.5 to 10 mM in the reaction mixture.

The present invention is further illustrated by the following examples. However, these examples are not to be construed to limit the scope of the invention.

EXAMPLE 1

[Determination of Conjugated Bilirubin]

Figure 1:
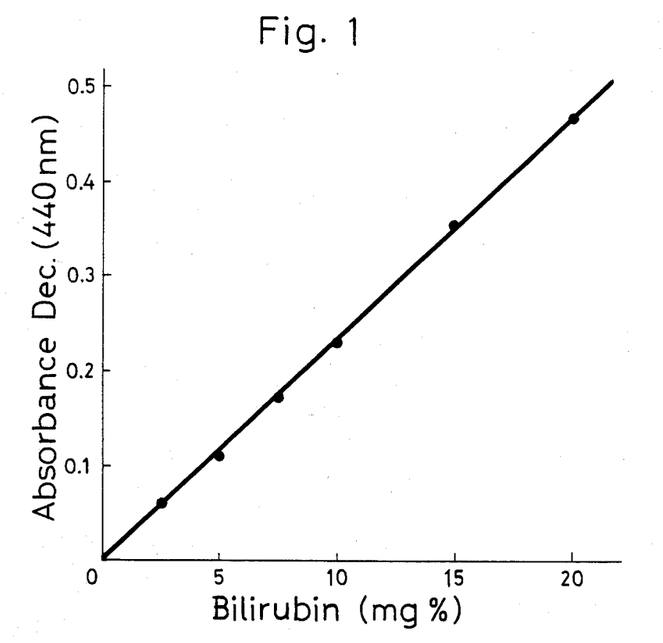
FIG. 1 illustrates the calibration curve obtained in Example 1 set forth hereinafter, the curve representing the relationship between bilirubin concentration and absorbance (decrease)

To 0.1 ml each of aqueous solutions of 0, 2.5, 5.0, 7.5, 10.0, 15.0 and 20.0 mg % bilirubin (crystals) was added 3 ml of a 0.1M tris-HCl buffer solution (pH 8.4) containing bilirubin oxidase of Myrothecium origin (0.1 U/ml). The resulting mixtures were incubated at 37° C. for 30 minutes and their absorbance decreases at 440 nm were then measured. The measured values were plotted against the corresponding concentrations of the said bilirubin solutions and a calibration curve as shown in FIG. 1 was obtained.

Then, 0.1 ml of a blood serum sample having an unknown bilirubin concentration (falling within the said range of 0 to 20 mg %; hereinafter the same) was reacted in the same manner as described above, and the absorbance decrease of the resulting reaction mixture was measured. By comparing the measured value with the calibration curve of FIG. 1, the (conjugated) bilirubin concentration in the sample was calculated and was found to be 2.8 mg %.

EXAMPLE 2

[Determination of Total Bilirubin]

To 0.1 ml each of aqueous solutions of 0, 2.5, 5.0, 7.5, 10.0, 15.0 and 20.0 mg % bilirubin (crystals) was added 3 ml of a buffer solution containing bilirubin oxidase of Myrothecium origin (0.1 U/ml) and sodium cholate (14 mM). The resulting mixtures were incubated at 37° C. for 30 minutes and their absorbance decreases at 440 nm were then measured. The measured values were plotted against the corresponding concentrations of the said bilirubin solutions, whereby a calibration curve quite similar to FIG. 1 was obtained.

Then, 0.1 ml of a blood serum sample having an unknown bilirubin concentration was reacted in the same manner as described above, and the absorbance decrease of the resulting reaction mixture was measured. By comparing the measured value with the calibration curve of FIG. 1, the (total) bilirubin concentration in the sample was calculated and found to be 5.2 mg %.

EXAMPLE 3

[Determination of Total Bilirubin]

The procedure of Example 2 was repeated except that bilirubin oxidase of Coprinus origin (3 mU/ml), laccase of Polyporus origin (0.1 mU/ml) or laccase of lacquer plant origin (1 mU/ml) was used in place of the bilirubin oxidase of Myrothecium origin. As a result, a calibration curve similar to FIG. 1 was obtained in each case, and the total bilirubin concentration in the sample was found to be 5.3 mg %, 5.2 mg % and 5.1 mg %, respectively.

EXAMPLE 4

[Determination of Glucose in Blood Serum]

Figure 2:
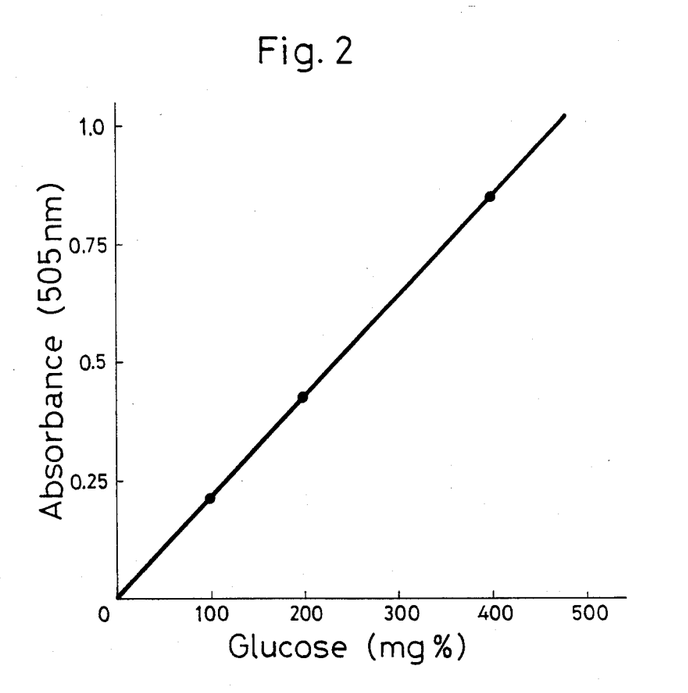
FIG. 2 illustrates the calibration curve obtained in Example 4 set forth hereinafter, the curve representing the relationship between glucose concentration and absorbance.

To 0.02 ml each of aqueous solutions of 0, 100, 200 and 400 mg % glucose was added 3 ml of a 0.1M phosphate buffer solution (pH 7.5) containing the reagents for use in the conventional method for the determination of glucose in biological fluids, i.e. 4-aminoantipyrine (0.4 mM), phenol (15 mM), glucose oxidase (17 U/ml) and peroxidase (0.3 U/ml), as well as bilirubin oxidase of Myrothecium origin (0.1 U/ml) and sodium cholate (14 mM). The resulting mixtures were incubated at 37° C. for 20 minutes and their absorbances at 505 nm were then measured. The measured values were plotted against the corresponding concentrations of the said glucose solutions and a calibration curve as shown in FIG. 2 was obtained.

Then, 0.02 ml of a blood serum sample having an unknown glucose concentration (and a total bilirubin concentration of 12.5 mg %) was subjected to reaction in the same manner as described above, and the absorbance of the resulting reaction mixture was measured. By comparing the measured value with the calibration curve of FIG. 2, the glucose concentration in the sample was calculated and found to be 96.1 mg %. As a control test, the above procedure was repeated except that the use of bilirubin oxidase and sodium cholate was omitted, whereby the glucose concentration in the sample was found to be 90.2 mg %. The above procedure was repeated once more, except that sodium fluoride (1 mM) was added to the reaction system further, whereby although the shape of the calibration curve and the found value of glucose concentration in the sample were substantially the same as those obtained in the present Example, the blank test value was so low as to have been convenient in the step of the absorbance measurement of the reaction mixtures.

EXAMPLE 5

[Determination of Glucose in Blood Serum]

The procedure of Example 4 was repeated except that bilirubin oxidase of Coprinus origin (3 mU/ml), laccase of Polyporus origin (0.1 mU/ml) or laccase of lacquer plant origin (1 mU/ml) was used in place of the bilirubin oxidase of Myrothecium origin. As a result, a calibration curve similar to FIG. 2 was obtained in each case, and the glucose concentration in the sample was found to be 95.8 mg %, 96.2 mg % and 95.9 mg %, respectively.

EXAMPLE 6

[Determination of Total Cholesterol in Blood Serum]

Figure 3:
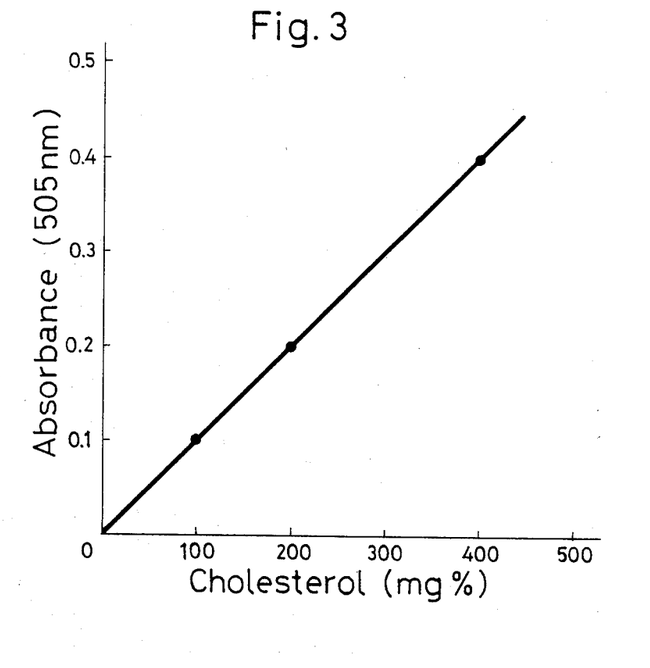
FIG. 3 illustrates the calibration curve obtained in Example 6 set forth hereinafter, the curve representing the relationship between cholesterol concentration and absorbance.

To 0.02 ml each of dioxane solutions of 0, 100, 200 and 400 mg % cholesterol (crystal) was added 3 ml of a 0.1M phosphate buffer solution (pH 7.5) containing the reagents for use in the conventional method for the determination of total cholesterol in biological fluids, i.e. 4-aminoantipyrine (0.4 mM), phenol (15 mM, cholesterol esterase (1 U/ml), cholesterol oxidase (2 U/ml), peroxidase (6.0 U/ml) and Triton X-100 [trademark; mfd. by Wako Pure Chem. Ind. Ltd.] (0.1%), as well as bilirubin oxidase of Myrothecium origin (0.1 U/ml), sodium dodecyl sulfate (2.5 mM) and sodium fluoride (2.5 mM). The resulting mixtures were incubated at 37° C. for 20 minutes and their absorbances at 505 nm were then measured. The measured values were plotted against the corresponding concentrations of the said cholesterol solutions and a calibration curve as shown in FIG. 3 was obtained.

Then, 0.02 ml of a blood serum sample having an unknown total cholesterol concentration (and a total bilirubin concentration of 15.2 mg %) was subjected to reaction in the same manner as above, and the absorbance of the resulting reaction mixture was measured. By comparing the measured value with the calibration curve of FIG. 3, the total cholesterol concentration in the sample was calculated and found to be 163 mg %. As a control test, the above procedure was repeated except that the use of bilirubin oxidase, sodium dodecyl sulfate and sodium fluoride was omitted, whereby the total cholesterol concentration in the sample was found to be 145 mg %.

EXAMPLE 7

[Determination of Total Cholesterol in Blood Serum]

The procedure of Example 6 was repeated except that bilirubin oxidase of Coprinus origin (3 mU/ml), laccase of Polyporus origin (0.1 mU/ml) or laccase of lacquer plant origin (1 mU/ml) was used in place of the bilirubin oxidase of Myrothecium origin. As a result, a calibration curve similar to that of FIG. 3 was obtained in each case, and the total cholesterol concentration in the sample was found to be 160 mg %, 163 mg % and 160 mg %, respectively.

EXAMPLE 8

[Determination of Neutral Fats (as Triolein) in Blood Serum]

Figure 4:
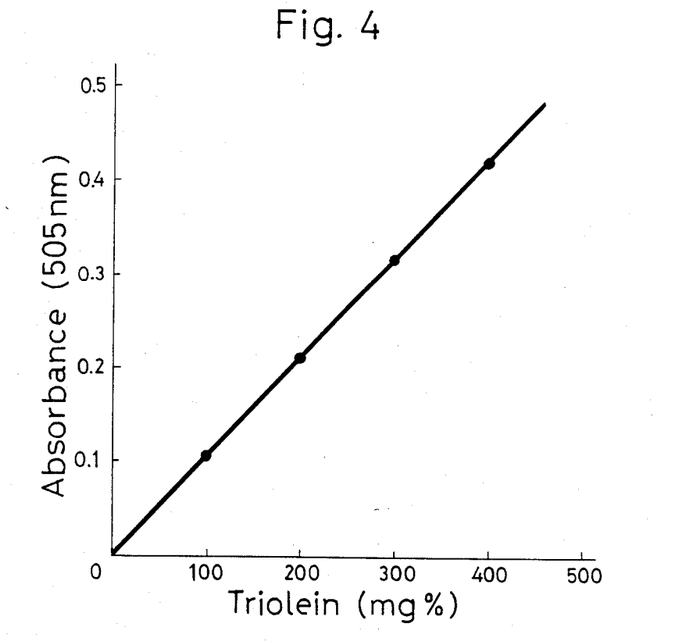
FIG. 4 illustrates the calibration curve obtained in Example 8 set forth hereinafter, the curve representing the relationship between triolein concentration and absorbance.

To 0.02 ml each of acetone solutions of 0, 100, 200, 300 and 400 mg % triolein (oil) was added 3 ml of a 0.1M tris buffer solution (pH 7.5) containing the reagents for use in the conventional method for the determination of neutral fats in biological fluids, i.e. 4-aminoantipyrine (0.4 mM), phenol (15 mM), lipoprotein lipase (200 U/ml), glycerol kinase (0.3 U/ml), glycerol-3-phosphate oxidase (4 U/ml), peroxidase (2 U/ml), adenosine triphosphate (0.8 mM) and Triton X-100 (0.1%), as well as bilirubin oxidase of Coprinus origin (0.05 U/ml), sodium cholate (14 mM) and phenanthroline (2.5 mM). The resulting mixtures were incubated at 37° C. for 20 minutes and their absorbances at 505 nm were then measured. The measured values were plotted against the corresponding concentrations of the said triolein solutions and a calibration curve as shown in FIG. 4 was obtained.

Then, 0.02 ml of a blood serum sample having an unknown neutral fat concentration (and a total bilirubin concentration of 14.2 mg %) was subjected to reaction in the same manner as described above, and the absorbance of the resulting reaction mixture was measured. By comparing the measured value with the calibration curve of FIG. 4, the neutral fat concentration in the sample was calculated and found to be 78.0 mg % as expressed by triolein. As a control test, the above procedure was repeated except that the use of bilirubin oxidase, sodium cholate and phenanthroline was omitted, whereby the neutral fat concentration in the sample was found to be 68.6 mg %.

EXAMPLE 9

[Determination of Free Fatty Acids (as Oleic Acid) in Blood Serum]

Figure 5:
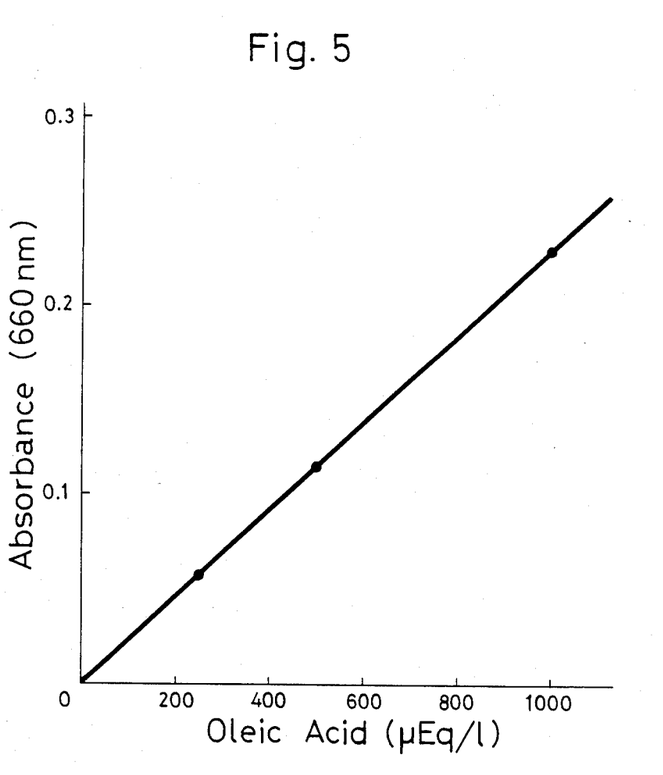
FIG. 5 illustrates the calibration curve obtained in Example 9 set forth hereinafter, the curve representing the relationship between oleic acid concentration and absorbance.

To 0.02 ml each of ethanolic solutions of 0, 250, 500 and 1000 $\mu$Eq/l oleic acid (oil) was added 3 ml of a buffer solution (pH 6.75) containing the reagents for use in the conventional method for the determination of free fatty acids in biological fluids, i.e. acylcoenzyme A synthetase (0.4 U/ml), acylcoenzyme A oxidase (5 U/ml), peroxidase (5 U/ml), adenosine triphosphate (4 $\mu$M), coenzyme A (0.5 $\mu$M), Color Former-MMX [trademark; mfd. by Kyowa-Medix Co.] (50 $\mu$M) and Triton X-100 (0.1%), as well as bilirubin oxidase of Myrothecium origin (0.1 U/ml), sodium cholate (14 mM) and sodium fluoride (2.5 mM). The resulting mixtures were incubated at 37° C. for 10 minutes and their absorbances at 660 nm were then measured. The measured values were plotted against the corresponding concentrations of the said oleic acid solutions and a calibration curve as shown in FIG. 5 was obtained.

Then, 0.02 ml of a blood serum sample having an unknown free fatty acid concentration (and a total bilirubin concentration of 10.8 mg %) was subjected to reaction in the same manner as described above, and the absorbance of the resulting reaction mixture was measured. By comparing the measured value with the calibration curve of FIG. 5, the free fatty acid concentration in the sample was calculated and found to be 210 $\mu$Eq/l as expressed by oleic acid. As a control test, the above-described procedure was repeated except that the use of bilirubin oxidase, sodium cholate and sodium fluoride was omitted, whereby the free fatty acid concentration in the sample was found to be 182 $\mu$Eq/l.

EXAMPLE 10

[Determination of Phospholipids (as Choline Chloride) in Blood Serum]

Figure 6:
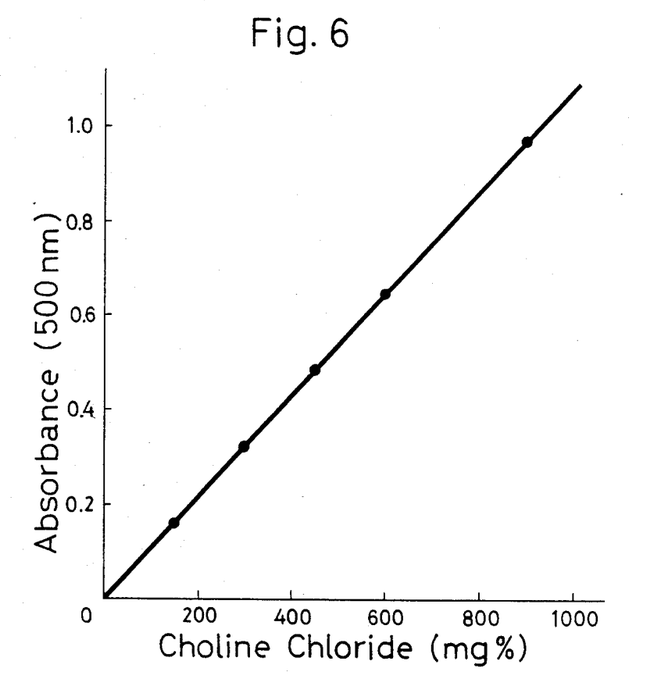
FIG. 6 illustrates the calibration curve obtained in Example 10 set forth hereinafter, the curve representing the relationship between choline chloride concentration and absorbance.

To 0.02 ml each of aqueous solutions of 0, 150, 300, 450, 600 and 900 mg % choline chloride (powder) was added 3 ml of a 0.1M phosphate buffer solution (pH 7.0) containing the reagents for use in the conventional method for the determination of phospholipids in biological fluids, i.e. 4-aminoantipyrine (0.4 mM), phenol (15 mM), phospholipase D (800 U/ml), choline oxidase (1 U/ml) and peroxidase (2 U/ml), as well as bilirubin oxidase of Coprinus origin (0.05 U/ml), sodium dodecyl sulfate (2.5 mM) and phenanthroline (2.5 mM). The resulting mixtures were incubated at 37° C. for 20 minutes and their absorbances at 500 nm were then measured. The measured values were plotted against the corresponding concentrations of the said choline chloride solutions and a calibration curve as shown in FIG. 6 was obtained.

Then, 0.02 ml of a blood serum sample having an unknown phospholipid concentration (and a total bilirubin concentration of 14.1 mg %) was subjected to reaction in the same manner as described above, and the absorbance of the resulting reaction mixture was measured. By comparing the measured value with the calibration curve of FIG. 6, the phospholipid concentration in the sample was calculated and found to be 277 mg % as expressed by choline chloride. As a control test, the above procedure was repeated except that the use of bilirubin oxidase, sodium dodecyl sulfate and phenanthroline was omitted, whereby the phospholipid concentration in the sample was found to be 262 mg %.

What is claimed is:

1. In the method for the quantitative determination of an unknown concentration of a physiological component selected from the group consisting of glucose, cholesterol, neutral fats, free fatty acids, phospholipids and uric acid present in a biological fluid which comprises:
   (a) reacting said component with an oxidizing enzyme in the presence of a color producing reagent, wherein the improvement comprises:
   (b) pretreating or treating said biological fluid at an alkaline pH without the formation of $H_2O_2$, under conditions and for a sufficient amount of time to remove bilirubin with a second enzyme selected from the group consisting of Myrothecium sp. bilirubin oxidase, Coprinus sp. bilirubin oxidase, lacquer plant laccase and basidiomycete laccase, together with
   (c) at least one additive agent selected from the group consisting of surface active agents, aromatic carboxylic acids, sulfa drugs, and proteases.

2. Method of claim 1 wherein the reacting in step (a) and the reacting is carried out in the presence of at least one counterpart interference reaction preventing compound selected from the group consisting of sodium fluoride, phenanthroline and hydroxylamine, in an amount sufficient for preventing interfering reaction between said second enzyme and said color producing reagent present in the reaction mixture.

3. Method of claim 2, wherein said oxidizing enzyme is correspondingly selected from the group consisting of glucose oxidase, cholesterol oxidase, glycerol-3-phosphate oxidase, acylcoenzyme A oxidase, choline oxidase and uricase.

4. Method of claim 2, wherein said second enzyme is said bilirubin oxidase and said bilirubin oxidase is present in an amount sufficient for providing a concentration thereof in the corresponding reaction mixture equal to 0.003 to 0.40 U/ml, or said second enzyme is said laccase and said laccase is present in an amount sufficient for providing a concentration thereof in the corresponding reaction mixture equal to 0.06 to 7.0 mU/ml, one unit of U being the amount of the corresponding said second enzyme which oxidizes one micromole of bilirubin per minute.

5. Method of claim 2, wherein said additive agent is at least one additive agent selected from the group consisting of sodium cholate, taurocholic acid, sodium dodecyl sulfate, p-toluenesulfonic acid, salicylic acid and sulfosalicylic acid.

6. Method of claim 5, wherein said additive agent is sodium dodecyl sulfate and is present in an amount sufficient for providing a concentration of 0.5 to 10 mM thereof in the corresponding reaction mixture.

7. Method of claim 5, wherein said additive agent is sodium cholate and is present in an amount sufficient for providing a concentration of 2 to 30 mM thereof in the corresponding reaction mixture.

8. Method of claim 2, wherein said counterpart interference reaction preventing compound is present in an amount sufficient for providing a concentration of 0.5 to 10 mM thereof in the corresponding reaction mixture.

9. Method of claim 1, wherein said oxidizing enzyme is correspondingly selected from the group consisting of glucose oxidase, cholesterol oxidase, glycerol-3-phosphate oxidase, acylcoenzyme A oxidase, choline oxidase and uricase.

10. Method of claim 1, wherein said second enzyme is said bilirubin oxidase and said bilirubin oxidase is present is an amount sufficient for providing a concentration thereof in the corresponding reaction mixture equal to 0.003 to 0.40 U/ml, or said second enzyme is said laccase and said laccase is present in an amount sufficient for providing a concentration thereof in the corresponding reaction mixture equal to 0.06 to 7.0 mU/ml, one unit of U being the amount of the corresponding said second enzyme which oxidizes 1 micromole of bilirubin per minute.

11. Method of claim 1, wherein said additive agent is at least one additive agent selected from the group consisting of sodium cholate, taurocholic acid, sodium dodecyl sulfate, p-toluenesulfonic acid, salicylic acid and sulfosalicylic acid.

12. Method of claim 11, wherein said additive agent is sodium dodecyl sulfate and is present in an amount sufficient for providing a concentration of 0.5 to 10 mM thereof in the corresponding reaction mixture.

13. Method of claim 11, wherein said additive agent is sodium cholate and is present in an amount sufficient for providing a concentration of 2 to 30 mM thereon in the corresponding reaction mixture.

14. A method for the quantitative determination of an unknown concentration of physiological component selected from the group consisting of glucose, cholesterol, neutral fats, free fatty acids, phospholipids, and uric acic present in a biological fluid which comprises:
   (a) treating said biological fluid at an alkaline pH without the formation of $H_2O_2$ under conditions and for a sufficient amount of time to remove bilirubin with a first enzyme selected from the group consisting of Myrothecium sp. bilirubin oxidase, Coprinus sp. bilirubin oxidase, lacquer plant laccase and basidiomycete laccase, together with
   (b) at least one additive agent selected from the group consisting of sodium cholate, taurocholic acid, sodium dodecyl sulfate, p-toluenesulfonic acid, salicylic acid and sulfosalicylic acid, and
   (c) reacting said component with an oxidizing enzyme selected from the group consisting of glucose oxidase, cholesterol oxidase, uricase, acylcoenzyme A oxidase, choline oxidase and glycerol-3-phosphate oxidase in the presence of color-producing substances.

15. Method of claim 14, wherein, at least one counterpart interference reaction preventing compound selected from the group consisting of sodium fluoride, phenanthroline and hydroxylamine is added to the corresponding reaction mixture in an amount sufficient to prevent interfering reaction between said first enzyme and said color producing substances present in the reaction mixture.

16. Method of claim 14 or 15 wherein the amount of said bilirubin oxidase or of said laccase is such that its concentration in the corresponding reaction mixture is equal to 0.003 to 0.40 U/ml for said bilirubin oxidase or 0.06 to 7.0 mU/ml for said laccase, the symbol U representing a unit of the corresponding first enzyme activity which unit is defined as the amount of the corresponding said first enzyme which oxidizes 1 micromole of bilirubin per minute, upon mixing a 2 ml portion of a solution, which has been prepared by dissolving 5 mg of bilirubin crystals in 250 ml of a 0.2M tris-HCl buffer solution of pH 8.4 containing 1 mM of ethylenediaminetetraacetic acid, with 0.2 ml of a solution of the corresponding said first enzyme, then incubating the resulting reaction mixture at 37° C. and measuring the absorbance decrease at 440 nm of the so incubated reaction mixture.

17. Method of claim 16 wherein said additive agent is sodium dodecyl sulfate and is used in such an amount as to give a concentration of 0.5 to 10 mM in the corresponding reaction mixture.

18. Method of claim 16 wherein said additive agent is sodium cholate and is used in such an amount as to give a concentration of 2 to 30 mM in the corresponding reaction mixture.

19. Method of claim 15 wherein said counterpart interference reaction preventing compound is used in such an amount as to give a concentration of 0.5 to 10 mM in the corresponding reaction mixture.

* * * * *